United States Patent [19]

Smith et al.

[11] Patent Number: 5,232,896
[45] Date of Patent: Aug. 3, 1993

[54] HERBICIDAL 2-(PHENOXY OR PHENYLTHIO)-2-(,3,5-TRIAZINYLOXY) ALKANOIC ACIDS

[75] Inventors: Michael G. Smith, Walnut Creek; William C. Lo, Hercules; Wendy S. Jacks, Walnut Creek; Robert J. Ehr, Vallejo, all of Calif.

[73] Assignee: DowElanco, Indianapolis, Ind.

[21] Appl. No.: 879,472

[22] Filed: May 6, 1992

Related U.S. Application Data

[62] Division of Ser. No. 692,742, Apr. 29, 1991.

[51] Int. Cl.$^5$ .................. A01N 43/66; C07D 251/30
[52] U.S. Cl. ..................... 504/212; 544/194; 544/208; 544/209; 544/211; 544/212; 544/213; 544/217; 544/218; 544/219
[58] Field of Search ........... 71/93; 544/194, 208, 544/209, 211, 212, 213, 217, 218, 219

[56] References Cited

U.S. PATENT DOCUMENTS 4,348,221  9/1982  Szczepanski et al. ............... 71/94
4,968,340 11/1990 Kaku et al. ....................... 71/92

FOREIGN PATENT DOCUMENTS 59-88470   5/1984  Japan.
1-301668  12/1989  Japan.

OTHER PUBLICATIONS

Linser, *Chemical Abstracts*, 53,20313f (1959).

*Primary Examiner*—Mukund J. Shah
*Assistant Examiner*—Y. N. Gupta
*Attorney, Agent, or Firm*—D. Wendell Osborne

[57] ABSTRACT

2-(Phenoxy or phenylthio)-2-(pyrimidinyloxy or 1,3,5-triazinyloxy)alkanoic acid compounds, such as ethyl 2-(2-fluorophenoxy)-2-(4,6-dimethylpyrimidin-2-yloxy)-acetate, were prepared by the reaction of a phenol or thiophenol compound with a 2-chloro-2-(pyrimidinyloxy or 1,3,5-triazinyloxy)alkanoate ester compound or by the reaction of a pyrimidinol or 1,3,5-triazinol with a 2-bromo-2-(phenoxy or phenylthio)alkanoate ester. These compounds, and, especially, agriculturally acceptable salts, esters, and amides of these compounds, were found to have herbicidal utility.

16 Claims, No Drawings

HERBICIDAL 2-(PHENOXY OR PHENYLTHIO)-2-(,3,5-TRIAZINYLOXY) ALKANOIC ACIDS

This is a division of application Ser. No. 07/692,742, filed Apr. 29, 1991.

BACKGROUND OF THE INVENTION

The present invention relates to substituted 2-(phenoxy or phenylthio)-2-(pyrimidinyloxy or 1,3,5-triazinyloxy)alkanoic acid compounds and their salts, esters, and amides, to herbicidal compositions containing these compounds, and to their use as herbicides.

The efficient production of quality food and fiber is highly dependent on the availability of effective herbicides that are safe to man and the environment to control undesirable vegetation. New compounds that are useful in this regard are continuously sought and when found highly prized.

Certain 2-(pyrimidinyloxy- and 1,3,5-triazinyloxy)alkanoic acids and their esters are known to possess herbicidal activity (see, for example, U.S. Pat. No. 4,968,340). Such compounds, however, generally lack the requisite high herbicidal activity and/or selectivity to crops and/or the low toxicity to man and the environment required to gain broad acceptance.

SUMMARY OF THE INVENTION

It has now been found that 2-(phenoxy or phenylthio)-2-(pyrimidinyloxy, or 1,3,5-triazinyloxy)alkanoic acid compounds are highly herbicidal, are selective toward valuable crops, and degrade in the environment at an acceptable rate.

The invention includes compounds of Formula I:

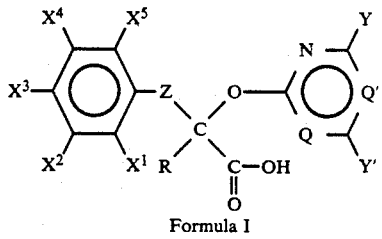

Formula I wherein

Q and Q' each independently represent N or C-Y''', with the proviso that at least one of Q and Q' represents N;

Y, Y', and Y''' each independently represent H, $R^1$, $OR^1$, $SR^1$, $NR^2_2$, F, Cl, or Br;

$X^1$ and $X^5$ each independently represent H, F, Cl, Br, or $(C_1-C_4)$alkyl optionally mono- or disubstituted with fluorine;

$X^2$ and $X^4$ each independently represent H, F, Cl, Br, $(C_1-C_4)$alkyl optionally mono- or disubstituted with fluorine, $SR^1$, $OR^1$, or O-phenyl, O-pyridinyl, or O-pyrimidinyl each optionally substituted with up to two substituents selected from F, Cl, Br, $CF_3$, $CH_3$, and CN;

$X^3$ represents H or F;

with the proviso that of $X^1$, $X^2$, $X^3$, $X^4$, and $X^5$ at least two represent H and at least three represent H or F;

Z represents O or S;

R represents H, $(C_1-C_3)$alkyl, $CO_2H$, CN, $CF_3$, or F;

$R^1$ represents $(C_1-C_3)$alkyl optionally singly to completely substituted with fluorine; and $R^2$ represents H or $(C_1-C_3)$alkyl;

or an agriculturally acceptable salt, ester, and amide thereof.

The compounds of Formula I and, especially, the agriculturally acceptable salts, esters, and amides thereof are combined with agriculturally acceptable adjuvants and carriers to prepare herbicical compositions.

The compounds of Formula I and their agriculturally acceptable salts, esters, and amides are useful as herbicides for the control of undesirable vegetation when applied either preemergence or postemergence and can be used to control undesirable vegetation in valuable crops by applying them to the undesirable vegetation or the locus thereof. The herbicidal effect is obtained whether a compound of Formula I, an agriculturally acceptable salt, ester, or amide thereof, or any other compound that degrades in the plant or in the environment to a compound of Formula I is applied. That is, undesirable vegetation is controlled by applying any compound that results in a compound of Formula I being present within the tissue of the undesirable vegetation. It is preferred to apply an agriculturally acceptable salt, ester, or amide of a compound of Formula I.

DETAILED DESCRIPTION OF THE INVENTION

The compounds of the invention are the compounds described by Formula I wherein Q and Q' each independently represent N or C-Y''' (with the proviso that at least one of Q and Q' represents N); Y, Y', and Y''' each independently represent H, $R^1$, $OR^1$, $SR^1$, $NR^2_2$, F, Cl, or Br; $X^1$ and $X^5$ each independently represent H, F, Cl, Br, or $(C_1-C_4)$alkyl optionally mono- or disubstituted with fluorine; $X^2$ and $X^4$ each independently represent H, F, Cl, Br, $(C_1-C_4)$alkyl optionally mono- or disubstituted with fluorine, $SR^1$, $OR^1$, or O-phenyl, O-pyridinyl, or O-pyrimidinyl each optionally substituted with up to two substituents selected from F, Cl, Br, $CF_3$, $CH_3$, and CN; $X^3$ represents H or F; with the proviso that of $X^1$, $X^2$, $X^3$, $X^4$, and $X^5$ at least two represent H and at least three represent H or F; Z represents O or S; R represents H, $(C_1-C_3)$alkyl, $CO_2H$, CN, $CF_3$, or F; $R^1$ represents $(C_1-C_3)$alkyl optionally singly to completely substituted with fluorine; and $R^2$ represents H or $(C_1-C_3)$alkyl; and the agriculturally acceptable salts, esters, and amides of these compounds. The base compounds can be described as 2-phenoxy-2-((2- or 4-)pyrimidinyloxy or 2-(1,3,5-triazinyloxy))alkanoic acids optionally possessing selected substituents on the phenyl, pyrimidinyl, triazinyl, and alkanoic acid moieties.

Compounds of Formula I wherein each of $X^1$, $X^2$, $X^3$, $X^4$, and $X^5$ represents H (unsubstituted phenyl compounds); wherein $X^1$ represents F and $X^2$, $X^3$, $X^4$, and $X^5$ represent H (2-fluorophenyl compounds); wherein $X^2$ represents F and $X^1$, $X^3$, $X^4$, and $X^5$ represent H (3-fluorophenyl compounds); wherein $X^1$ and one of $X^4$ and $X^5$ represent F and $X^2$, $X^3$ and the other of $X^4$ and $X^5$ represent H (2,6-, and 2,5-difluorophenyl compounds) are often preferred. Compounds wherein Z represents O are usually preferred (acetal compounds) as are compounds wherein R represents H (acetic acid compounds). Compounds wherein Q represents N and Q' represents C-H (pyrimidin-2-yl compounds) are preferred in some circumstances and compounds wherein both Q and Q' represent N (1,3,5-triazin-2-yl compounds) are preferred in other circumstances. Compounds of Formula I wherein Y, Y', and Y" each independently represent H, CH$_3$, or OCH$_3$ are also often preferred. Those wherein Y and Y' both represent CH$_3$ and Y", if present, represents H and are typically more preferred. It is usually preferred to employ the acid compounds of Formula I in the form of an agriculturally acceptable ester. Such esters include (C$_1$–C$_8$)alkyl and (C$_3$–C$_8$)alkoxyalkyl esters. Specifically preferred compounds include the methyl, ethyl, propyl, and butyl esters of 2-(2-fluorophenoxy)-2-(4,6-dimethylpyrimidin-2-yloxy)acetic acid, 2-(3-fluorophenoxy)-2-(4,6-dimethylpyrimidin-2-yloxy)acetic acid, 2-(2,6-difluorophenoxy)-2-(4,6-dimethylpyrimidin-2-yloxy)acetic acid, 2-(2,5-difluorophenoxy-2-(4,6-dimethylpyrimidin-2-yloxy)acetic acid; 2-(2-fluorophenoxy)-2-(4-methyl-6-methoxypyrymidin-2-yloxy)acetic acid, and 2-(2-fluorophenoxy)-2-(4,6-dimethyl-1,3,5-triazin-2-yloxy)acetic acid.

The compounds of Formula I exist in two enantiomeric isomer forms because the carbon atom adjacent to the carboxylic acid moiety is asymmetrically substituted (except in the case where R represents CO$_2$H). The present invention relates to each of the enantiomeric isomers and to all mixtures of these isomers. It is anticipated that the enantiomeric isomers will both have utility as herbicides but that one of the enantiomeric isomers will be generally more efficacious than the other.

Agriculturally acceptable salts, esters, and amides are those salts, esters, and amides of the carboxylic acid group(s) of Formula I which have a cation, OR$^3$, NH$_2$, NHR$^3$, or NR$^3{}_2$ moiety that is not itself significantly herbicidal to any crop being treated nor significantly deleterious to the applicator, the environment, or the ultimate user of any crop being treated.

Suitable cations include, for example, those derived from alkali or alkaline earth metals and those derived from ammonia and amines. Preferred cations include sodium, potassium, magnesium, and aminium cations of the formula $$R^5R^6R^7NH\oplus$$

wherein R$^5$, R$^6$, and R$^7$ each, independently represents hydrogen or (C$_1$–C$_{12}$)alkyl, (C$_3$–C$_{12}$)cycloalkyl, or (C$_3$–C$_{12}$)alkenyl, each of which is optionally substituted by one or more hydroxy, (C$_1$–C$_8$)alkoxy, (C$_1$–C$_8$)alkylthio or phenyl groups, provided that R$^5$, R$^6$, and R$^7$ are sterically compatible. Additionally, any two of R$^5$, R$^6$, and R$^7$ together may represent an aliphatic difunctional moiety containing 1 to 12 carbon atoms and up to two oxygen or sulfur atoms. Salts of the compounds of Formula I can be prepared by treatment of compounds of Formula I or an ester thereof with a metal hydroxide, such as sodium hydroxide, potassium hydroxide, or magnesium hydroxide, or by treatment of a compound of Formula I with an amine, such as ammonia, triethylamine, dimethylamine, hydroxyethylamine, trisallylamine, 2-butoxyethylamine, morpholine, cyclodedecylamine, or benzylamine.

Suitable esters and amides include those wherein each R$^3$ independently represents (C$_1$–C$_8$)alkyl or (C$_3$–C$_8$)alkenyl, each optionally substituted with up to 3 compatible groups selected from (C$_1$–C$_4$)alkoxy, F, Cl, Br, and phenyl, or phenyl optionally substituted with up to 3 groups selected from F, Cl, Br, CH$_3$, or CF$_3$. (C$_1$–C$_4$)Alkyl esters are generally preferred and methyl and butyl esters are often specifically preferred.

The invention further contemplates the control of undesirable vegetation by treating the vegetation or its locus with a substance that degrades in the environment or in the undesirable vegetation to a compound of Formula I. The application of such compounds in place of a compound of Formula I into the tissue of the undesirable vegetation and, thereby to realize the herbicidal action of the compound of Formula I. Many such compounds can be envisioned. Thus, those compounds that are readily oxidized or hydrolyzed in the environment or in plant tissue to a compound of Formula I, such as, for example, compounds wherein the carboxylic acid moiety is replaced by hydroxymethyl, aminoethyl, formyl, 2-carboxyethyl, 5-chloro-2-pentenyl, cyano, 2-dioxolanyl, can all be employed. The critical feature is that the substance applied places a compound of Formula I within the plant tissue.

The compounds of Formula I can be prepared by the reaction of a hydroxy substituted heterocycle of Formula II with an optionally substituted 2-halo-2-phenoxyalkanoate or 2-halo-2-(phenylthio)alkanoate ester of Formula III.

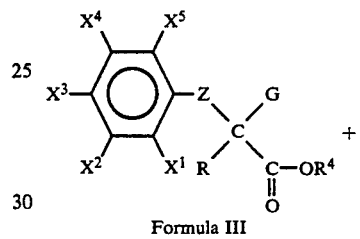

Formula III

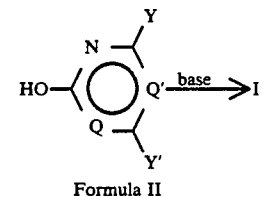

Formula II

R$^4$ of Formula III represents (C$_1$–C$_8$)alkyl or (C$_3$–C$_8$)alkoxyalkyl. Methyl or ethyl esters are often preferred for general operations and when the ultimate preparation of a specific ester of a compound of Formula I is desired, it is preferred to employ the same ester of the compound of Formula III. G represents bromine or chlorine, most generally bromine. The reaction is generally carried out by first converting an appropriate substituted pyrimidinol or 1,3,5-triazinol to its alkali metal salt by treatment with a strong base, such as sodium hydride, potassium carbonate, or a tetraalkylammonium hydroxide in an inert solvent, such as tetrahydrofuran or N,N-dimethylformamide, and then adding an optionally substituted 2-halo-2-(phenoxy or phenylthio)alkanoate ester and allowing the two to react. An ester of a compound of Formula I is formed which can be recovered by conventional means. This ester can be converted to an acid compound of Formula I or to a salt thereof by hydrolysis, to a different ester by transesterification, or to an amide by treatment with an amine, all using conventional methods well known in the art.

Optionally substituted 2-bromo-(2-phenoxy)alkanoate and 2-bromo-2-(phenylthio)alkanoate esters of Formula III wherein X$^1$ and X$^5$ each independently represent H, F, Cl, Br, or (C$_1$–C$_4$)alkyl optionally mono- or disubstituted with fluorine; X$^2$ and X$^4$ each independently represent H, F, Cl, Br, (C$_1$–C$_4$)alkyl optionally mono- or disubstituted with fluorine, $SR^1$, $OR^1$, or O-phenyl, O-pyridinyl, or )-pyrimidinyl each optionally substituted with up to two substituents selected from F, Cl, Br, $CF_3$, $CH_3$, and CN; $X^3$ represents H or F; with the proviso that of $X^1$, $X^2$, $X^3$, $X^4$, and $X^5$ at least two represent H and at least three represent H or F; $R^1$ represents $(C_1–C_3)$alkyl optionally singly to completely substituted with fluorine; Z represents O or S; R represents H, $(C_1–C_3)$alkyl, $CO_2H$, CN, $CF_3$, or F; and $R^4$ represents $(C_1–C_8)$alkyl or $(C_3–C_8)$alkoxyalkyl that are useful as starting materials for the above-described process can be prepared by bromination of the corresponding optionally substituted 2-phenoxyalkanoate ester of 2-(phenylthio)alkanoate ester with N-bromosuccinimide by procedures well known in the art.

Alternately, the compounds of Formula I can be prepared by the reaction of an optionally substituted phenol or thiophenol with an optionally substituted 2-halo-2-(heterocyclyloxy)alkanoate ester of Formula IV wherein R, $R^4$, Q, Q', Y, Y', and G are as defined hereinbefore.

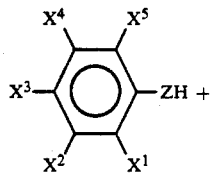

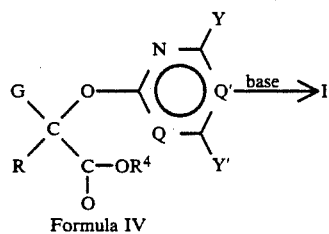

Formula IV

The reaction can be carried out by adding the optionally substituted phenol or thiophenol and a base, such as sodium hydride or potassium carbonate, to the optionally substituted 2-halo-2-(heterocyclyloxy)alkanoate ester in a solvent, such as tetrahydrofuran, acetonitrile, or N,N-dimethylformamide. The product obtained, which is an ester of a compound of Formula I, can be recovered by conventional means.

The optionally substituted 2-halo-2-(heterocyclyloxy)alkanoate esters of Formula IV wherein Y, Y', and Y'' each independently represent H, $R^1$, $OR^1$, $SR^1$, $NR^2_2$, F, Cl, or Br; $R^1$ represents $(C_1–C_3)$alkyl optionally singly to completely substituted with fluorine; R represents H, $(C_1–C_3)$alkyl, $CO_2H$, CN, $CF_3$, or F; and $R^4$ represents $(C_1–C_8)$alkyl or $(C_3–C_8)$alkoxyalkyl that are useful as starting materials required for the above-described process can be prepared by chlorination or bromination of an appropriate optionally substituted 2-(heterocyclyloxy)alkanoate ester. This can be accomplished by consecutively adding lithium hexamethyldisilylamide and the appropriate (2-heterocyclyloxy)alkanoate ester to a dry-ice and acetone cooled solution of trimethylsilyl chloride in an ether solvent, such as diethyl ether or tetrahydrofuran, and then adding N-chlorosuccinimide or N-bromosuccinimide with stirring and cooling. The 2-halo-2-(heterocyclyloxy)alkanoate ester prepared can be recovered by removing the water soluble and volatile components of the product mixture by extraction and evaporation or by other conventional methods. These compounds are typically employed as intermediates without further purification.

The 2-(heterocyclyloxy)alkanoate esters employed in the process described above can be prepared either by the reaction of an appropriate 2-hydroxyalkanoate ester with an appropriate chloro or methanesulfonyl substituted pyrimidine or 1,3,5-triazine or by the reaction of an appropriate pyrimidinol or 1,3,5-triazinol with an ester of an appropriate 2-bromoalkanoic acid. Suitable reaction conditions for such processes are well known in the art.

The compounds of the present invention can be used directly as herbicides, but it is generally preferable to first prepare an herbicidal composition containing one or more of the compounds in combination with an agriculturally acceptable adjuvant or carrier. Suitable adjuvants or carriers should not be phytotoxic to valuable crops, particularly at the concentrations employed in applying the compositions for selective weed control in the presence of crops, and should not react chemically with compounds of Formula I or other composition ingredients. Such mixtures can be designed for application directly to plants or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene perchloroethylene, ethyl acetate, amyl acetate, butyl acetate, propylene glycol monomethyl ether and diethylene glycol monomethyl ether, isopropyl alcohol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, actionic, or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate, alkylnaphthalenesulfonate salts, such as sodium dibutylnaphthalenesulfonate; dialkyl esters of sulfoccuinate salts, such as sodium di(2-ethylhexyl) sulfoccinate; sorbitol esters, such as sorbitol oleate; quaternary amines, such as lauryl trimethylammonium chloride polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorant, penetration aids, spreading agents, sticking agents, dispersing agents, thickening agents, freeze point depressants, antimicrobial agents, and the like. The addition of crop oil and crop oil concentrates is typical. The compositions can also contain other compatible components, for example, other herbicides, plant growth regulators, fungicides, insecticides, and the like and can be formulated with solid, particulate fertilizer carriers such as ammonium nitrate, urea, and the like or with liquid fertilizers.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably from about 10 to about 90 weight percent. Such compositions are typically diluted with an inert carrier, such as water, before application. The diluted compositions usually applied to plants or their locus generally contain from about 0.001 to about 5 weight percent active ingredient and preferably contain from about 0.01 to about 1.0 percent. It is preferred to employ an agriculturally acceptable salt, ester, or amide of a compound of Formula I in herbicidal compositions because such compounds are generally much more stable than are the acids of Formula I.

The present compositions can be applied by the use of conventional ground or aerial dusters and sprayers, by addition to irrigation water, and by other conventional means known to those skilled in the art.

The compounds of the present invention can be used for general vegetation control at higher application rates or can be employed at lower rates wherein desirable vegetation is unaffected, but undesirable vegetation is controlled. They are especially valuable for the control of undesirable vegetation in the presence of crop plants. The selective control of undesirable vegetation in cereal crops, especially in wheat and barley crops, is preferred with most of the compounds and the selective control of undesirable vegetation in corn is preferred with a few.

General herbicide action is usually observed for compounds of Formula I, including the agriculturally acceptable salts, esters, and amides thereof, at rates of greater than about 2 Kg/Ha for preemergence and 1 Kg/Ha for postemergence applications. The selective control of susceptible weeds in crops such as wheat and corn can be accomplished at application rates of from about 500 g/Ha to about 1 Kg/Ha preemergence and of from about 10 g/Ha to about 500 g/Ha postemergence. An appropriate rate for each crop, compound and circumstance can be determined by simple range finding tests using the teachings herein.

The term "herbicide" is used herein to mean an active ingredient which controls or adversely modifies growth of plants. By "vegetation controlling" or "herbicidally effective" amount is meant an amount of active ingredient which causes an adversely modifying effect and includes deviations from natural development, killing, regulation, dessication, retardation, and the like. The terms "plants" and "weeds" are meant to include germinant seeds, emerging seedlings, and established vegetation. "Undesirable vegetation" is plant life present in a place where it is not wanted.

Herbicidal activity is exhibited by the compounds of the present invention when they are applied directly to the plant or to the locus of the plant at any stage of growth or before emergence. The effect observed depends upon the plant species to be controlled, the stage of growth of the plant, the application parameters of dilution and the spray drop size, the particle size of solid components, the environmental conditions at the time of use, the specific compound employed, the specific adjuvants and carriers employed, and the like, as well as the amount of chemical applied. These and other factors can be adjusted as is known in the art to promote selective herbicidal action. It is preferred to employ the compounds of Formula I and their agriculturally acceptable salts, esters, and amides to control undesirable vegetation by postemergence application.

EXAMPLES

Example 1

Preparation of Methyl 2-Bromo-2-phenoxyacetate

Methyl phenoxyacetate (5.0 g, 30 mmol), N-bromosuccinimide (5.4 g, 30 mmol), a few crystals (0.2 to 0.5 g) of benzoyl peroxide, and 50 mL of carbon tetrachloride were placed in a 100 ml flask and heated at reflux with stirring for about 4 hr. The mixture was then allowed to cool, was filtered, and was concentrated by evaporation under reduced pressure to obtain 6.6 g (90 percent of theory) of the title compound as a red oil.

H$^1$ NMR ($\delta$, CDCl$_3$), 3.91 (s, 3H), 6.57 (s, 1H), 7.07–7.60 (m, 5H).

Example 2

Preparation of Methyl 2-Phenoxy-2-(4,6-dimethylpyrimidin-2-yl)oxy)acetate 4,6-Dimethyl-2-pyrimidinol (3.0 g, 24 mmol) and 60 mL of tetrahydrofuran were placed in a dry 250 mL flask and blanketed with argon. Sodium hydride (1.0 g of 60 percent, 24 mmol) was added carefully and the mixture was allowed to stir at ambient temperature for 0.5 hr. A solution of methyl 2-bromo-2-phenoxyacetate (7.2 g, 29 mmol) in a small amount of tetrahydrofuran was added dropwise with stirring and the mixture was then allowed to stir overnight under argon at ambient temperature. The resulting mixture was found by thin layer chromatography to contain only a trace of the starting pyrimidinol. The mixture was concentrated by evaporation under reduced pressure and the residue was diluted with water and ether. The phases that formed were separated and the aqueous phase was extracted twice with ether. The combined ethereal phase was extracted with water and then dried over magnesium sulfate, filtered, and concentrated by evaporation under reduced pressure to obtain the title compound in crude form as a reddish oil. This oil was column chromatographed on silica eluting with a 75:25 mixture of hexane and ethyl acetate to obtain 1.2 g (17 percent of theory) of the title compound as a pink oil of 93 percent purity, as determined by gas-liquid chromatography.

$^1$H NMR ($\delta$, CDCl$_3$), 2.4 (s, 6H), 3.86 (s, 3H), 6.78 (s, 1H), 6.82 (s, 1H), 7.01–7.52 (m, 5H);

$^{13}$C NMR (δ, CDCl$_3$), 23.8, 52.9, 93.3, 115.5, 117.5, 123.4, 129.6, 156.4, 162.4, 166.5, 169.6.

Alternately, the tetrabutylammonium salt of 4,6-dimethyl-2-pyrimidinol was first prepared by placing 4,6-dimethyl-2-hydroxypyrimidine (13.0 g, 0.105 mol) in a flask, adding 65 g of 40 percent aqueous tetrabutylammonium hydroxide (0.10 mol), and removing the water by evaporation under reduced pressure at pressures down to about 10 mm Hg (1.33 kPa) at 40°-45° C. The residue amounted to 42.7 g and appeared to be a dihydrate of the desired salt. A 10.9 g portion of this (25 mmol) was placed in a 500 mL flask containing 25 mL of tetrahydrofuran. A cloudy solution formed. To this was added with stirring at ambient temperature 14 mL of a solution of methyl 2-bromo-2-phenoxyacetate in tetrahydrofuran (containing about 25 mmol). The resulting mixture was allowed to stir for 2 days. Analysis by gas-liquid chromatography indicated only one significant compound was present. A 250 mL portion of diethyl ether was added and the resulting mixture was extracted 5 times with 100 mL portions of water and then with brine. The ethereal solution was dried over magnesium sulfate, filtered, and concentrated by evaporation under reduced pressure to obtain the title compound in crude form as a dark brown oil. This was filtration chromatographed on silica gel eluting first with a 10:90 mixture of diethyl ether and hexane and then with a 15:85 mixture of ethyl acetate and hexane. The product containing eluate was concentrated by evaporation under reduced pressure to obtain 2.50 g (35 percent of theory) of the title compound as a pale yellow oil. This oil solidified on standing to a light orange solid melting at 50°-53° C.

Example 3

Preparation of Ethyl 2-(4,6-Dimethyl-2-pyrimidinyloxy)acetate

A solution containing 4,6-dimethyl-2-methylsulfonylpyrimidine (10.0 g, 53.8 mmol), ethyl glycolate (5.60 g, 53.8 mmol), and 30 mL of N,N-dimethylformamide was prepared and to this was added with stirring potassium carbonate (8.0 g, 60 mmol). The mixture was allowed to stir at ambient temperature overnight. It was then poured into water and the resulting mixture was extracted 3 times with ethyl acetate. The combined organic extracts were extracted with water. The aqueous extract was saturated with sodium chloride and extracted twice more with ethyl acetate. All of the ethyl acetate layers were combined, dried over magnesium sulfate, filtered, and concentrated by evaporation under reduced pressure to obtain 8.20 g (72.6 percent of theory) of the title compound as a yellow oil. This oil was filtration chromatographed on silica gel, eluting with a 30:70 mixture of ethyl acetate and hexane. The product containing eluate was concentrated by evaporation under reduced pressure to obtain 7.9 g (70 percent of theory) of the title compound as a colorless oil which solidified on standing to a white solid melting at 57°-59° C.

Example 4

Preparation of Ethyl 2-Chloro-2-(4,6-dimethyl-2-pyrimidinyloxy)acetate

A solution of trimethylsilyl chloride (0.70 mL, 0.60 g, 5.5 mmol) and ethyl 2-(4,6-dimethyl-2-pyrimidinyloxy)acetate (1.0 g, 4.8 mmol) in 4 mL of tetrahydrofuran was prepared and cooled to −78° C. with a dry-ice/acetone bath and to this was added with stirring a 1M solution of lithium hexamethyldisilylamide in tetrahydrofuran (5.5 mL, 5.5 mmol). The solution, which became yellowish orange, was stirred for 15 minutes and then N-chlorosuccinimide (0.70 g, 5.2 mmol) was added with stirring and cooling. After a few minutes the mixture was allowed to warm and about 50 mL of hexane was added. The resulting solution was extracted with water three times, dried over magnesium sulfate, and concentrated by evaporation under reduced pressure to obtain a pasty oil. This was redissolved in hexane and the resulting solution filtered and concentrated under reduced pressure to obtain 0.65 g of the title compound as a yellow oil that was about 63 percent pure as determined by gas-liquid chromatography.

Example 5

Preparation of Methyl 2-(3-Phenoxyphenoxy)-2-(4,6-dimethyl-2-pyrimidinyloxy)acetate 3-Phenoxyphenol (1.0 g, 5.4 mmol) was placed in a flask with potassium carbonate (0.90 g, 6.5 mmol) and 20 mL of acetonitrile and to this was added dropwise with stirring at ambient temperature, a solution of ethyl 2-chloro-2-(4,6-dimethyl-2-pyrimidinyloxy)acetate (1.40 g, 5.7 mmol) in 5 mL of acetonitrile. The mixture was allowed to stir overnight and was then added to water and the resulting mixture was extracted 3 times with ether. The ethereal solution was extracted 2 times with 1N aqueous sodium hydroxide, dried over magnesium sulfate, filtered, and concentrated by evaporation under reduced pressure to obtain about 1 g of the title compound as a crude yellow oil. This oil, which solidified on standing, was chromatographed on silica eluting with an 85:15 mixture of hexane and ethyl acetate to obtain 0.60 g (28 percent of theory) of the title compound as a white solid melting at 111°-112° C.

Example 6

Preparation of Sodium 2-(2-Fluorophenoxy-2-(4,6-dimethylpyrimidin-2-yloxy)acetate Ethyl 2-(2-fluorophenoxy-2-(4,6-dimethyl-2-pyrimidinyloxy)acetate (0.3 g, 0.94 mmol) was placed in a 25 mL flask with 10 mL of tetrahydrofuran and 0.84 mL (0.84 mmol) of 1N sodium hydroxide solution was added with stirring. The mixture was stirred at ambient temperature overnight after which only a trace of starting ester remained as determined by thin layer chromatography using silica and a 70:30 mixture of hexane and ethyl acetate. The mixture was concentrated by evaporation under reduced pressure and the residue diluted with water and ether. The aqueous and organic layers were separated and the aqueous layer was extracted twice with ether. It was then concentrated by evaporation under reduced pressure to obtain 0.25 g (85 percent of theory) of the title compound as a white solid.

The compounds listed in Table I were prepared by the methods described in Examples 2, 5, and 6 as indicated in Table I. The proton nuclear magnetic resonance absorptions of a number of the ester and amide products are given in Table Ia.

TABLE I
EXAMPLES OF COMPOUNDS OF THE INVENTION

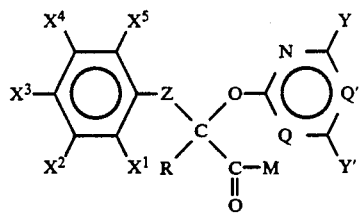

| Cpd No. | $X^1$, $X^2$, $X^3$, $X^4$ & $X^5$ (other than H) | Y, Y' & Y'' (other than H) | Z | M | Q | Q' | R | Made by Ex. No. | Yield, Percent | Form | Melting Point, °C. | Elemental Analysis, Percent Calc./Found C | H | N |
|---|---|---|---|---|---|---|---|---|---|---|---|---|---|---|
| 1 | — | Y = CH$_3$<br>Y' = CH$_3$ | O | OCH$_3$ | N | C—H | H | 2 | 35 | orange solid | 50–53 | 62.5<br>62.3 | 5.59<br>5.74 | 9.72<br>9.57 |
| 2 | — | Y = CH$_3$<br>Y' = CH$_3$ | O | ONa | N | C—H | H | 6 | | white solid | 168–170 | | | |
| 3 | $X^1$ = F | Y = CH$_3$<br>Y' = CH$_3$ | O | OC$_2$H$_5$ | N | C—H | H | 2 | 28 | yellow oil | | 60.0<br>59.7 | 5.31<br>5.36 | 8.75<br>8.59 |
| 4 | $X^1$ = F | Y = CH$_3$<br>Y' = CH$_3$ | O | ONa | N | C—H | H | 6 | | white solid | 149–151 (d) | | | |
| 5 | $X^2$ = F<br>$X^4$ = F | Y = CH$_3$<br>Y' = CH$_3$ | O | OC$_2$H$_5$ | N | C—H | H | 2 | 15 | yellow oil | | 56.8<br>56.8 | 4.73<br>4.62 | 8.28<br>8.00 |
| 6 | $X^2$ = F<br>$X^4$ = F | Y = CH$_3$<br>Y' = CH$_3$ | O | ONa | N | C—H | H | 6 | | white solid | 144–146 | | | |
| 7 | $X^1$ = F<br>$X^3$ = F | Y = CH$_3$<br>Y' = CH$_3$ | O | OC$_2$H$_5$ | N | C—H | H | 2 | 13 | yellow oil | | 56.8<br>56.6 | 4.73<br>4.82 | 8.28<br>8.15 |
| 8 | $X^1$ = F<br>$X^3$ = F | Y = CH$_3$<br>Y' = CH$_3$ | O | ONa | N | C—H | H | 6 | | white solid | 129–132 | | | |
| 9 | $X^2$ = F<br>$X^3$ = F | Y = CH$_3$<br>Y' = CH$_3$ | O | OC$_2$H$_5$ | N | C—H | H | 2 | 17 | yellow oil | | 56.8<br>57.0 | 4.73<br>4.72 | 8.28<br>7.99 |
| 10 | $X^2$ = F<br>$X^3$ = F | Y = CH$_3$<br>Y' = CH$_3$ | O | ONa | N | C—H | H | 6 | | white solid | 129–132 | | | |
| 11 | $X^1$ = F<br>$X^4$ = F | Y = CH$_3$<br>Y' = CH$_3$ | O | OC$_2$H$_5$ | N | C—H | H | 2 | 26 | yellow oil | | 56.8<br>56.7 | 4.73<br>4.62 | 8.28<br>8.09 |
| 12 | $X^1$ = F<br>$X^4$ = F | Y = CH$_3$<br>Y' = CH$_3$ | O | ONa | N | C—H | H | 6 | | white solid | 115–118 | | | |
| 13 | $X^1$ = F<br>$X^2$ = F | Y = CH$_3$<br>Y' = CH$_3$ | O | OC$_2$H$_5$ | N | C—H | H | 2 | 20 | yellow oil | | 56.8<br>56.5 | 4.73<br>4.67 | 8.28<br>7.95 |
| 14 | $X^1$ = F<br>$X^2$ = F | Y = CH$_3$<br>Y' = CH$_3$ | O | ONa | N | C—H | H | 6 | | white solid | 150–153 | | | |
| 15 | $X^1$ = F<br>$X^5$ = F | Y = CH$_3$<br>Y' = CH$_3$ | O | OC$_2$H$_5$ | N | C—H | H | 2 | 18 | yellow oil | | 56.8<br>55.7 | 4.73<br>4.59 | 8.28<br>8.12 |
| 16 | $X^1$ = F<br>$X^5$ = F | Y = CH$_3$<br>Y' = CH$_3$ | O | ONa | N | C—H | H | 6 | | white solid | 134–136 (d) | | | |
| 17 | $X^3$ = F | Y = CH$_3$<br>Y' = CH$_3$ | O | OC$_2$H$_5$ | N | C—H | H | 2 | 28 | yellow oil | | 60.0<br>60.0 | 5.31<br>5.18 | 8.75<br>8.53 |
| 18 | $X^3$ = F | Y = CH$_3$<br>Y' = CH$_3$ | O | ONa | N | C—H | H | 6 | | lt. brown solid | 120–124 (d) | | | |
| 19 | $X^2$ = F | Y = CH$_3$<br>Y' = CH$_3$ | O | OC$_2$H$_5$ | N | C—H | H | 2 | 15 | orange oil | | 60.0<br>59.7 | 5.31<br>5.28 | 8.75<br>8.66 |
| 20 | $X^2$ = F | Y = CH$_3$<br>Y' = CH$_3$ | O | ONa | N | C—H | H | 6 | | yellow solid | 130–133 | | | |
| 21 | $X^1$ = Cl | Y = CH$_3$<br>Y' = CH$_3$ | O | OC$_2$H$_5$ | N | C—H | H | 2 | 14 | yellow oil | | 57.1<br>56.8 | 5.05<br>5.14 | 8.32<br>8.23 |
| 22 | $X^1$ = Cl | Y = CH$_3$<br>Y' = CH$_3$ | O | ONa | N | C—H | H | 6 | | white solid | 176–180 (d) | | | |
| 23 | $X^1$ = Br | Y = CH$_3$<br>Y' = CH$_3$ | O | OC$_2$H$_5$ | N | C—H | H | 2 | 9 | yellow oil | | 50.4<br>50.0 | 4.46<br>4.35 | 7.35<br>7.32 |
| 24 | $X^1$ = Br | Y = CH$_3$<br>Y' = CH$_3$ | O | ONa | N | C—H | H | 6 | | white solid | 181–184 (d) | | | |
| 25 | $X^1$ = Cl | Y = CH$_3$<br>Y' = CH$_3$ | O | OC$_2$H$_5$ | N | C—H | H | 2 | 67 | colorless oil | | 52.1<br>51.8 | 4.61<br>4.54 | 7.60<br>7.59 |
| 26 | $X^1$ = Cl | Y = CH$_3$<br>Y' = CH$_3$ | O | OH | N | C—H | H | 6 | | white solid | 141(d) | | | |
| 27 | $X^1$ = F | Y = CH$_3$<br>Y' = CH$_3$ | O | OC$_2$H$_5$ | C—H | N | H | 2 | 19 | yellow oil | | 60.0<br>60.0 | 5.35<br>5.34 | 8.75<br>8.66 |
| 28 | $X^1$ = F | Y = CH$_3$<br>Y' = CH$_3$ | O | ONa | C—H | N | H | 6 | | white solid | 204–207 (d) | | | |
| 29 | — | Y = OCH$_3$<br>Y' = OCH$_3$ | O | OC$_2$H$_5$ | N | C—H | H | 2 | 40 | white solid | 55–60 | 56.2<br>56.5 | 5.04<br>5.44 | 8.75<br>8.48 |
| 30 | — | Y = OCH$_3$<br>Y' = OCH$_3$ | O | ONa | N | C—H | H | 6 | | white solid | 157–160 | | | |
| 31 | $X^2$ = Cl | Y = CH$_3$<br>Y' = CH$_3$ | O | OC$_2$H$_5$ | N | C—H | H | 2 | 9 | yellow oil | | 57.1<br>56.8 | 5.05<br>5.02 | 8.32<br>8.17 |

TABLE I-continued
EXAMPLES OF COMPOUNDS OF THE INVENTION

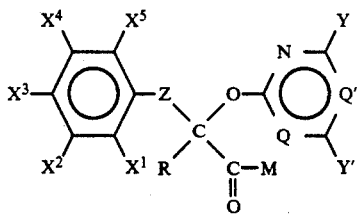

| Cpd No. | $X^1, X^2, X^3, X^4$ & $X^5$ (other than H) | $Y, Y'$ & $Y''$ (other than H) | Z | M | Q | Q' | R | Made by Ex. No. | Yield, Percent | Form | Melting Point, °C. | Elemental Analysis, Percent Calc./Found C | H | N |
|---|---|---|---|---|---|---|---|---|---|---|---|---|---|---|
| 32 | $X^2$ = Cl | Y = $CH_3$ Y' = $CH_3$ | O | ONa | N | C—H | H | 6 | | white solid | 143–145 (d) | | | |
| 33 | $X^2$ = F | Y = $CH_3$ Y' = $CH_3$ | S | $OC_2H_5$ | N | C—H | H | 2 | 26 | orange oil | | 57.1 57.4 | 5.10 5.32 | 8.33 8.34 |
| 34 | $X^2$ = F | Y = $CH_3$ Y' = $CH_3$ | S | ONa | N | C—H | H | 6 | | yellow crystals | 101–105 | | | |
| 35 | $X^2$ = Br | Y = $CH_3$ Y' = $CH_3$ | O | $OC_2H_5$ | N | C—H | H | 2 | 17 | yellow oil | | 50.4 50.3 | 4.50 4.33 | 7.35 7.06 |
| 36 | $X^2$ = Br | Y = $CH_3$ Y' = $CH_3$ | O | ONa | N | C—H | H | 6 | | amber glass | | | | |
| 37 | $X^2$ = F | Y = $OCH_3$ Y' = $OCH_3$ | S | $OC_2H_5$ | N | C—H | H | 2 | 7 | clear oil | | 52.2 52.0 | 4.65 4.28 | 7.61 7.70 |
| 38 | $X^2$ = F | Y = $OCH_3$ Y' = $OCH_3$ | S | ONa | N | C—H | H | 6 | | white powder | 146–149 | | | |
| 39 | $X^1$ = F | Y = $CH_3$ Y' = $CH_3$ | O | $OC_2H_5$ | N | C—H | H | 2 | 5 | orange oil | | 58.8 59.0 | 4.94 4.87 | 9.15 8.57 |
| 40 | $X^1$ = F | Y = $CH_3$ Y' = $CH_3$ | O | $NHCH_3$ | N | C—H | H | | | white solid | 128–129 | | | |
| 41 | $X^1$ = F | Y = $CH_3$ Y' = $CH_3$ | O | $OCH_3$ | N | C—H | H | | 12 | colorless oil | | 58.8 59.0 | 4.90 5.00 | 9.15 9.07 |
| 42 | $X^1$ = F | Y = $CH_3$ Y' = $CH_3$ | O | $OC_8C_{17}$ (n) | N | C—H | H | 2 | 3 | colorless oil | | 63.4 64.7 | 7.18 7.49 | 6.93 6.30 |
| 43 | $X^1$ = F | Y = $CH_3$ Y' = $CH_3$ | O | $NH_2$ | N | C—H | H | 2 | 70 | white solid | 139 | 57.7 57.6 | 4.81 4.95 | 14.4 14.2 |
| 44 | $X^1$ = F | Y = $CH_3$ Y' = $CH_3$ | O | $N(CH_3)_2$ | N | C—H | H | | 23 | white solid | 110–111 | 60.2 60.0 | 5.64 5.79 | 13.2 13.2 |
| 45 | $X^1$ = F $X^5$ = F | Y = $OCH_3$ Y' = $OCH_3$ | O | $OC_2H_5$ | N | C—H | H | 2 | 21 | white solid | 64–66 | 51.9 51.4 | 4.36 4.51 | 7.57 7.39 |
| 46 | $X^1$ = F $X^5$ = F | Y = $CH_3$ Y' = $CH_3$ | O | $OC_2H_5$ | C—H | N | H | 2 | 39 | clear oil | | 56.8 56.5 | 4.77 5.03 | 8.28 8.07 |
| 47 | $X^1$ = F $X^5$ = F | Y = $OCH_3$ Y' = $OCH_3$ | O | ONa | N | C—H | H | 6 | | white solid | | | | |
| 48 | $X^1$ = F $X^5$ = F | Y = $CH_3$ Y' = $CH_3$ | O | ONa | C—H | N | H | 6 | | white solid | 220–224 | | | |
| 49 | $X^2$ = F | Y = $OCH_3$ Y' = $OCH_3$ | O | $OC_2H_5$ | N | C—H | H | 2 | 20 | white solid | 63–64 | 54.5 54.4 | 4.86 4.89 | 7.95 7.94 |
| 50 | $X^2$ = F | Y = $OCH_3$ Y' = $OCH_3$ | O | ONa | N | C—H | H | 6 | | white solid | 195–197 | | | |
| 51 | $X^1$ = F | Y = $OCH_3$ Y' = $OCH_3$ | O | $OC_2H_5$ | N | C—H | H | 2 | 28 | white solid | 74–76 | 54.5 54.5 | 4.86 4.92 | 7.95 7.58 |
| 52 | $X^1$ = F | Y''' = Cl | O | $OC_2H_5$ | N | C—Y'' | H | 2 | 23 | colorless oil | | 51.5 51.5 | 3.70 3.82 | 8.57 8.59 |
| 53 | $X^1$ = F | Y = $CH_3$ Y' = $CH_3$ | S | ONa | N | C—H | H | 6 | | beige powder | 45–55 | | | |
| 54 | $X^1$ = F | Y = $CH_3$ Y' = $CH_3$ | S | $OC_2H_5$ | N | C—H | H | 2 | 18 | brown oil | | 57.1 57.0 | 5.10 5.07 | 8.33 7.95 |
| 55 | — | Y = $CH_3$ Y' = $CH_3$ | S | $OC_2H_5$ | N | C—H | H | 2 | 8 | yellow oil | | 60.4 59.9 | 5.66 5.68 | 8.81 8.65 |
| 56 | — | Y = $CH_3$ Y' = $CH_3$ | S | ONa | N | C—H | H | 6 | | off-white solid | 138–141 (d) | | | |
| 57 | $X^1$ = F | Y = $OCH_3$ Y' = $OCH_3$ | O | $OC_2H_5$ | N | N | H | 2 | 65 | pale green oil | | 51.0 51.3 | 4.56 4.87 | 11.9 11.7 |
| 58 | $X^1$ = F | Y = $OCH_3$ Y' = $OCH_3$ | O | $OC_2H_5$ | N | C—H | H | 2 | 29 | pale oil | | 57.1 57.3 | 5.09 5.12 | 8.33 8.11 |
| 59 | $X^1$ = F | Y = $CH_3$ Y' = $CH_3$ | O | NHOH | N | C—H | H | | 63 | brown solid | 100–104 (d) | 54.7 54.8 | 4.56 4.97 | 13.7 12.4 |
| 60 | $X^2$ = $OC_6H_5$ | Y = $CH_3$ Y' = $CH_3$ | O | $OC_2H_5$ | N | C—H | H | 5 | 27 | white solid | 111–112 | 67.0 67.2 | 5.58 5.73 | 7.11 7.08 |
| 61 | $X^2$ = $OCH_3$ | Y = $CH_3$ Y' = $CH_3$ | O | $OC_2H_5$ | N | C—H | H | 5 | 51 | yellow oil | | 61.4 61.4 | 6.07 6.29 | 8.43 8.40 |
| 62 | $X^1$ = $CH_3$ | Y = $CH_3$ Y' = $CH_3$ | O | $OC_2H_5$ | N | C—H | H | 5 | 40 | yellow | | 64.6 | 6.33 | 8.86 |

TABLE I-continued
EXAMPLES OF COMPOUNDS OF THE INVENTION

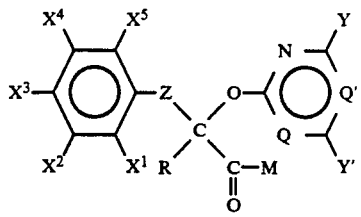

| Cpd No. | $X^1, X^2, X^3, X^4$ & $X^5$ (other than H) | Y, Y' & Y'' (other than H) | Z | M | Q | Q' | R | Made by Ex. No. | Yield, Percent | Form | Melting Point, °C. | Elemental Analysis, Percent Calc./Found C | H | N |
|---|---|---|---|---|---|---|---|---|---|---|---|---|---|---|
| 63 | $X^2$ = $CH_3$ | Y' = $CH_3$<br>Y = $CH_3$ | O | $OC_2H_5$ | N | C—H | H | 5 | 40 | oil<br>yellow oil | | 64.2<br>64.6 | 6.43<br>6.33 | 8.74<br>8.86 |
| 64 | $X^1$ = F | Y' = $CH_3$<br>$Y^1$ = $OC_2H_5$<br>$Y^2$ = $CH_3$ | O | $OC_2H_5$ | N | C—H | H | 2 | | clear oil | | 64.3 | 6.66 | 8.90 |
| 65 | $X^2$ = $SCH_3$ | Y = $CH_3$<br>Y' = $CH_3$ | O | $OC_2H_5$ | N | C—H | H | 5 | 17 | yellow oil | | 58.6<br>58.6 | 5.75<br>5.95 | 8.05<br>8.04 |
| 66 | $X^1$ = Br<br>$X^5$ = Br | Y = $CH_3$<br>Y' = $CH_3$ | O | $OC_2H_5$ | N | C—H | H | 5 | 46 | white solid | 103.5–104.5 | 41.8<br>42.0 | 3.51<br>3.66 | 6.09<br>6.13 |
| 67 | $X^1$ = F | Y = $CH_3$<br>Y' = $CH_3$ | O | $OC_2H_5$ | N | N | H | 2 | 29 | pale oil | | 56.1<br>56.1 | 5.02<br>5.21 | 13.1<br>12.9 |
| 68 | $X^2$ = O(5-$CF_3$-2-$C_5H_3N$ | Y = $CH_3$<br>Y' = $CH_3$ | O | $OC_2H_5$ | N | C—H | H | | | | | | | |
| 69 | $X^1$ = Cl<br>$X^5$ = Cl | Y = $CH_3$<br>Y' = $CH_3$ | O | $OC_2H_5$ | N | C—H | H | | | | | | | |
| 70 | $X^1$ = F<br>$X^5$ = Cl | Y = $CH_3$<br>Y' = $CH_3$ | O | $OC_2H_5$ | N | C—H | H | | | | | | | |
| 71 | $X^1$ = F | Y = Cl<br>Y' = $CH_3$ | O | $OC_2H_5$ | N | C—H | H | | | | | | | |
| 72 | $X^1$ = F | Y = Cl<br>Y' = $OCH_3$ | O | $OC_2H_5$ | N | C—H | H | | | | | | | |
| 73 | $X^1$ = F | Y = $OCH_3$ | O | $OC_2H_5$ | N | C—H | H | | | | | | | |
| 74 | $X^1$ = F | Y = $OCHF_2$<br>Y' = $OCHF_2$ | O | $OC_2H_5$ | N | C—H | H | | | | | | | |
| 75 | $X^1$ = F | Y = $OCHF_2$<br>Y' = $CH_3$ | O | $OC_2H_5$ | N | C—H | H | | | | | | | |
| 76 | $X^1$ = F | Y = $CH_2F$<br>Y' = $CH_3$ | O | $OC_2H_5$ | N | C—H | H | | | | | | | |
| 77 | $X^1$ = F | Y = $CF_3$<br>Y' = $CH_3$ | O | $OC_2H_5$ | N | C—H | H | | | | | | | |
| 78 | $X^1$ = F | Y'' = $CH_3$ | O | $OC_2H_5$ | N | C—Y'' | H | | | | | | | |
| 79 | $X^1$ = F | Y'' = Cl | O | $OC_2H_5$ | N | C—Y'' | H | | | | | | | |
| 80 | $X^1$ = F | Y = $CH_3$<br>Y'' = Cl | O | $OC_2H_5$ | N | C—Y'' | H | | | | | | | |
| 81 | $X^1$ = F | Y = $CH_3$<br>Y''' = $CH_3$ | O | $OC_2H_5$ | N | C—Y'' | H | | | | | | | |
| 82 | $X^1$ = F | Y = $CH_3$<br>Y' = $OCH_3$ | O | $OC_2H_5$ | N | N | H | | | | | | | |
| 83 | $X^1$ = F | Y = $OCH_3$<br>Y' = Cl | O | $OC_2H_5$ | N | N | H | | | | | | | |
| 84 | $X^1$ = F | Y = $CH_3$<br>Y' = Cl | O | $OC_2H_5$ | N | N | H | | | | | | | |
| 85 | $X^1$ = F | Y = $CH_3$ | O | $OC_2H_5$ | N | N | H | | | | | | | |
| 86 | $X^1$ = F | Y = $OCH_3$ | O | $OC_2H_5$ | N | N | H | | | | | | | |
| 87 | $X^2$ = $OC_6H_4$—Cl(2) | Y = $C_2H_5$<br>Y' = $OC_2H_5$ | O | $OC_2H_4$—$OC_4H_9$ | C—H | N | $CH_3$ | | | | | | | |
| 88 | $X^2$ = $OC_6H_4$—$CF_3$(3) | Y = $CH_3$<br>Y' = $NHCH_3$ | O | $OC_2H_5$ | N | N | CN | | | | | | | |
| 89 | $X^2$ = $OC_6H_3$-diF(2,4) | Y = $OC_3H_7$<br>Y' = $C_3H_7$ | O | $N(CH_3)$ $OCH_3$ | C—H | N | $CF_3$ | | | | | | | |
| 90 | $X^1$ = F<br>$X^2$ = $OC_6H_5$ | Y'' = $CH_3$ | O | $OCH_3$ | C—Y'' | N | $CO_2CH_3$ | | | | | | | |
| 91 | $X^1$ = F<br>$X^4$ = $OC_3H_7$ | — | S | $OC_3H_7$—$OCH_3$ | N | C—H | $C_2H_5$ | | | | | | | |

TABLE Ia

¹H NUCLEAR MAGNETIC RESONANCE ABSORPTION DATA

| Compound No. | δ, PPM From Tetramethylsilane (CDCl₃) |
|---|---|
| 1 | 2.35(s, 6H), 3.81(s, 3H), 6.71(s, 1H), 6.75(s, 1H), 7.0–7.3(m, 5H) |
| 3 | 1.2–1.35(t, 3H), 2.30(s, 6H), 4.2–4.35 (q, 2H), 6.67(s, 1H), 6.72(s, 1H), 6.85–7.30(m, 4H) |
| 5 | 1.2–1.35(t, 3H), 2.35(s, 6H), 4.2–4.35 (q, 2H), 6.4–6.8(m, 5H) |
| 7 | 1.2–1.35(t, 3H), 2.30(s, 6H), 4.2–4.35 (q, 2H), 6.65(s, 1H), 6.70(s, 1H), 6.71–7.25(m, 3H) |
| 9 | 1.2–1.35(t, 3H), 2.35(s, 6H), 4.2–4.35 (q, 2H), 6.63(s, 1H), 6.74(s, 1H), 6.80–7.15(m, 3H) |
| 11 | 1.2–1.35(t, 3H), 2.35(s, 6H), 4.2–4.35 (q, 2H), 6.6–7.1(m, 5H) |
| 13 | 1.2–1.35(t, 3H), 2.35(s, 6H), 4.2–4.35 (q, 2H), 6.72(s, 1H), 6.76(s, 1H), 6.8–7.1(m, 3H) |
| 15 | 1.2–1.35(t, 3H), 2.32(s, 6H), 4.20–4.40 (q, 2H), 6.65(s, 1H), 6.68(s, 1H), 6.75–7.10(m, 3H) |
| 17 | 1.2–1.35(t, 3H), 2.35(s, 6H), 4.2–4.35 (q, 2H), 6.62(s, 1H), 6.70(s, 1H), 6.85–7.15(m, 4H) |
| 19 | 1.2–1.35(t, 3H), 2.35(s, 6H), 4.2–4.35 (q, 2H), 6.70(s, 1H), 7.73(s, 1H), 6.75–7.28(m, 4H) |
| 21 | 1.2–1.35(t, 3H), 2.32(s, 6H), 4.21–4.38 (q, 2H), 6.68(s, 1H), 6.74(s, 1H), 6.9–7.4(m, 4H) |
| 23 | 1.2–1.35(t, 3H), 2.30(s, 6H), 4.20–4.40 (q, 2H), 6.69(s, 1H), 6.72(s, 1H), 6.85–7.55(m, 4H) |
| 25 | 1.2–1.35(t, 3H), 3.75(s, 6H), 4.25–4.40 (q, 2H), 5.72(s, 1H), 6.65(s, 1H), 6.93–7.40(m, 4H) |
| 27 | 1.29(t, 3H, J=7.0), 2.39(s, 3H), 2.40 (s, 3H), 4.31(q, 2H, J=7.0), 6.52(s, 1H), 6.84(s, 1H), 6.9–7.3(m, 4H) |
| 28 | 2.30(s, 3H), 2.32(s, 3H), 6.52(s, 1H), 6.60(s, 1H), 6.9–7.3(m, 4H) (DMSO) |
| 29 | 1.31(t, 3H, J=7.1), 4.33(q, 2H, J=7.1), 6.76(s, 1H), 6.8–7.3(m, 6H), 7.57(t, 1H, J=8.2) |
| 30 | 6.40(s, 1H), 6.8–7.3(m, 6H), 7.75(t, 1H, J=8.1) (DMSO) |
| 31 | 1.2–1.32(t, 3H), 2.32(s, 6H), 4.20–4.35 (q, 2H), 6.70(s, 1H), 6.73(s, 1H), 6.95–7.27(m, 4H) |
| 33 | 1.2–1.32(t, 3H), 2.32(s, 6H), 4.20–4.35 (q, 2H), 6.67(s, 1H), 6.74(s, 1H), 7.0–7.3(m, 4H) |
| 35 | 1.25–1.35(t, 3H), 2.38(s, 6H), 4.25–4.37 (q, 2H), 6.71(s, 1H), 6.75(s, 1H), 7.05–7.37(m, 4H) |
| 39 | 1.20–1.35(t, 3H), 2.4(s, 3H), 4.2–4.4 (q, 2H), 6.72(s, 1H), 6.85(d, 1H), 7.0–7.3 (m, 4H), 8.32(d, 1H) |
| 45 | 1.31(t, 3H, J=7.2), 2.72(s, 6H), 4.33 (q, 2H, J=7.2), 5,71(s, 1H), 6.66(s, 1H), 6.8–7.1(m, 3H) |
| 46 | 1.28(t, 3H, J=7.0), 2.24(s, 3H), 2.33 (s, 3H), 4.30(q, 2H, J=7.0), 6.47(s, 1H), 6.80(s, 1H), 6.7–7.0(m, 3H) |
| 49 | 1.25–1.35(t, 3H), 3.82(s, 6H), 4.25–4.38 (q, 2H), 5.57(s, 1H), 6.61(s, 1H), 6.72–6.92(m, 3H), 7.19–7.30(m, 1H) |
| 51 | 1.25–1.35(t, 3H), 3.78(s, 6H), 4.25–4.40 (q, 2H), 5.74(s, 1H), 6.67(s, 1H), 7.0–7.3(m, 4H) |
| 52 | 1.25–1.35(t, 3H), 4.25–4.44(q, 2H), 6.63 (s, 1H), 7.0–7.3(m, 4H), 8.44(s, 2H) |
| 54 | 1.15–1.9(t, 3H), 2.35(s, 6H), 4.06–4.14 (q, 2H), 6.50(s, 1H), 6.69(s, 1H), 7.0–7.4 (m, 3H), 7.6–7.8(m, 1H) |
| 55 | 1.05–1.12(t, 3H), 2.35(s, 6H), 4.00–4.15 (q, 2H), 6.50(s, 1H), 6.70(s, 1H), 7.2–7.7 (m, 5H) |
| 57 | 1.25–1.35(t, 3H), 3.95(s, 6H), 4.25–4.40 (q, 2H), 6.73(s, 1H), 7.0–7.3(m, 4H) |
| 58 | 1.25–1.35(t, 3H), 2.28(s, 3H), 3.80 (s, 3H), 4.25–4.4(q, 2H), 6.25(s, 1H), 6.73 (s, 1H), 7.0–7.3(m, 4H) |
| 59 | 2.23(s, 6H), 6.92(s, 1H), 7.0–7.3(m, 4H), 9.0–9.5(br s) (in DMSO) |
| 60 | 1.20–1.35(t, 3H), 2.35(s, 6H), 4.25–4.35 (q, 2H), 6.6–7.4(m, 11H) |
| 61 | 1.25–1.32(t, 3H), 2.38(s, 6H), 3.75 (s, 3H), 4.24–4.37(q, 2H), 6.57–6.77 (m, 5H), 7.11–7.20(t, 1H) |
| 62 | 1.2–1.35(t, 3H), 2.25(s, 3H), 2.35(s, 6H), 4.2–4.35(q, 2H), 6.65(s, 1H), 6.70(s, 1H), 6.85–7.2(m, 4H) |
| 63 | 1.2–1.35(t, 3H), 2.30(s, 3H), 2.35(s, 6H), 4.2–4.35(q, 2H), 6.67(s, 1H), 6.70(s, 1H), 6.8–7.2(m, 4H) |
| 65 | 1.2–1.35(t, 3H), 2.35(s, 6H), 2.40(s, 3H), 4.2–4.35(q, 2H), 6.70(s, 2H), 6.8–7.2 (m, 4H) |
| 66 | 1.32–1.40(t, 3H), 2.20(s, 6H), 4.32–4.45 (q, 2H), 6.65(s, 1H), 6.79–6.89(t, 1H), 6.98(s, 1H), 7.40–7.45(d, 2H) |
| 67 | 1.2–1.35(t, 3H), 2.50(s, 6H), 4.25–4.40 (q, 2H), 6.76(s, 1H), 7.0–7.3(m, 4H) |

Example 7

Postemergence Herbicidal Activity

Seeds of the desired test plant species were planted in sandy soil having a pH range of about 5–7.5 and an organic matter content of less than 0.5 percent in plastic pots with a surface area of 64 square cm. The plants were grown for 7–20 days in a greenhouse with an approximately 14 hr photoperiod maintained at about 25°–33° C. during the day and 15°–20° C. during the night. Nutrients were added on a regular basis and supplemental lighting was provided with an overhead 1000 Watt multi-vapor lamp when necessary. The plants were employed for testing after they reached the first or second true leaf-stage.

A weighed amount of each test compound in a 10 mL glass vial was dissolved in 4 mL of a 97:3 mixture of acetone and dimethyl sulfoxide to obtain concentrated stock solutions. If the test compound did not dissolve readily, the mixture was warmed and sonicated. The stock solutions obtained were diluted with an aqueous mixture containing acetone, water, isopropyl alcohol, dimethyl sulfoxide, Atplus 411F crop oil concentrate, and Triton X-155 surfactant in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by dilution of appropriate smaller portions of the stock solution. Approximately 1.5 mL aliquots of each solution of known concentration were sprayed evenly onto various test plants using a Cornwall TM glass syringe fitted with a Tee-Jet TM TN-3 hollow cone nozzle so as to obtain thorough coverage of each plant. Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants compared to that of the untreated plants was determined visually and scored on a scale of 0 to 100 percent, where 0 corresponds to no injury and 100 corresponds to complete kill. Some of the compounds tested, application rates employed, plant species tested, and results are given in Table II.

stock solutions. If the test compound did not dissolve readily, the mixture was warmed and sonicated. The stock solutions obtained were diluted with a 99.0:0.1 mixture of water and Tween TM 20 to obtain application solutions of known concentration. The solutions containing the highest concentration to be tested were prepared by diluting 4 mL aliquots of the stock solution with 8.5 mL of the mixture and lower concentrations were prepared by dilution of appropriate smaller portions of the stock solution. A 2.5 mL aliquot of each

TABLE II

| | | | | | | | | | | | | | | | |
|---|---|---|---|---|---|---|---|---|---|---|---|---|---|---|---|
| POSTEMERGENCE HERBICIDAL ACTIVITY | | | | | | | | | | | | | | | |
| Cpd. No. | Dose Rate, PPM | Cockle-bur | Jimson-weed | Lambs-quar-ters | Morn-ing-glory | Pig-weed | Vel-vet-leaf | Vero-nica | Wild buck-wheat | Black grass | Giant Fox-tail | John-son-grass | Wild oats | Corn | Wheat |
| 1 | 500 | 35 | 50 | 75 | 75 | 85 | 85 | 85 | 80 | 50 | 35 | 0 | 65 | 0 | 35 |
| 3 | 125 | 90 | 80 | 85 | 100 | 100 | 80 | — | 80 | 80 | 30 | 80 | 70 | 85 | 35 |
|   | 15 6 | 90 | 70 | 80 | 78 | 80 | 78 | — | 70 | 75 | 0 | 70 | 40 | 40 | 0 |
| 4 | 125 | 100 | 95 | 85 | 85 | 100 | 65 | 95 | 95 | 70 | 50 | 70 | 60 | 85 | 30 |
| 5 | 500 | 30 | 25 | 35 | — | 50 | 65 | 15 | 40 | 0 | 0 | 0 | 0 | 30 | 0 |
| 7 | 1000 | 75 | 35 | 70 | — | 80 | 45 | 50 | 75 | 25 | 0 | 0 | 0 | 0 | 0 |
| 9 | 1000 | 35 | 25 | 80 | — | 90 | 65 | 40 | 80 | 35 | 0 | 0 | 0 | 0 | 0 |
| 11 | 125 | 90 | 90 | 80 | 100 | 90 | 80 | 80 | 75 | 0 | 50 | 50 | 0 | 80 | 10 |
| 13 | 125 | 70 | 70 | 70 | 85 | 90 | 30 | 50 | 80 | 0 | 0 | 20 | 0 | 0 | 20 |
| 15 | 125 | 95 | 80 | 80 | 80 | 90 | 70 | — | 80 | 85 | 30 | 90 | 80 | 90 | 0 |
| 17 | 125 | 40 | 70 | 50 | 70 | 80 | 60 | 80 | 0 | 0 | 0 | 0 | 0 | 10 | 0 |
| 19 | 125 | 80 | 85 | 80 | 90 | 80 | 80 | — | 80 | 80 | 0 | 78 | 65 | 35 | 0 |
| 21 | 1000 | 100 | 90 | 80 | 90 | 100 | 98 | 100 | 95 | 80 | 70 | 50 | 30 | 85 | 0 |
| 23 | 500 | 85 | 75 | 85 | — | 95 | 80 | 95 | 95 | 0 | 0 | 0 | 0 | 20 | 0 |
| 25 | 2000 | 80 | 75 | 80 | 70 | 70 | 90 | 90 | 80 | 20 | 0 | 0 | 30 | 0 | 0 |
| 27 | 1000 | 80 | 70 | 80 | 90 | 90 | 70 | — | 80 | 40 | 0 | 70 | 0 | 20 | 40 |
| 29 | 1000 | 80 | 80 | 85 | 85 | 100 | 85 | 75 | 80 | 0 | 0 | 0 | 0 | 0 | 15 |
| 31 | 2000 | 90 | 80 | 70 | 90 | 90 | 80 | 70 | 98 | 40 | 0 | 0 | 0 | 50 | 0 |
| 33 | 1000 | 50 | 80 | 50 | 50 | 45 | 40 | 55 | 50 | 0 | 30 | 0 | 0 | 55 | 0 |
| 35 | 1000 | 65 | 75 | 85 | 85 | 95 | 50 | 55 | 85 | 0 | 0 | 0 | 0 | 10 | 0 |
| 37 | 1000 | 0 | 75 | 75 | 50 | 55 | 80 | 100 | 90 | 0 | 15 | 0 | 0 | 0 | 15 |
| 39 | 500 | 0 | 35 | 75 | 15 | 75 | 45 | 50 | 75 | 25 | 0 | 10 | 10 | 10 | 30 |
| 40 | 500 | 0 | 35 | 75 | 30 | 30 | 20 | 85 | 85 | 45 | 30 | 35 | 20 | 75 | 30 |
| 41 | 125 | 100 | 80 | 80 | 65 | 100 | 70 | 100 | 100 | 25 | 0 | 55 | 40 | 75 | 0 |
| 42 | 125 | 80 | 75 | 85 | 75 | 75 | 60 | 70 | 80 | 35 | 0 | 35 | 30 | 80 | 0 |
| 43 | 500 | 85 | 90 | 90 | 100 | 85 | 85 | 100 | 85 | 85 | 80 | 95 | 65 | 95 | 55 |
| 44 | 500 | 0 | 15 | 80 | 30 | 75 | 20 | 70 | 55 | 15 | 25 | 75 | 20 | 40 | 25 |
| 45 | 2000 | 80 | 95 | 90 | 25 | 100 | 90 | 95 | 90 | 35 | 25 | 50 | 15 | 40 | 15 |
| 46 | 1000 | 35 | 55 | 85 | 25 | 75 | 50 | 75 | 70 | 15 | 0 | 75 | 15 | 75 | 0 |
| 49 | 1000 | 85 | 100 | 90 | 75 | 95 | 85 | 95 | 90 | 15 | 0 | 0 | 10 | 25 | 0 |
| 51 | 1000 | 65 | 90 | 90 | 65 | 100 | 90 | 100 | 90 | 25 | 0 | 0 | 25 | 20 | 0 |
| 52 | 2000 | 0 | 0 | 80 | 0 | 30 | 85 | 35 | 25 | 15 | 0 | 0 | 0 | 0 | 0 |
| 54 | 1000 | 65 | 85 | 85 | 35 | 95 | 80 | 100 | 75 | 20 | 0 | 35 | 0 | 65 | 0 |
| 55 | 1000 | 60 | 20 | 0 | 70 | 40 | 65 | 50 | 20 | 0 | 0 | 0 | 0 | 0 | 0 |
| 57 | 2000 | 80 | 80 | 85 | 95 | 100 | 80 | 85 | 90 | 0 | 25 | 0 | 0 | 0 | 0 |
| 58 | 1000 | 95 | 100 | 95 | 100 | 100 | 95 | 100 | 95 | 50 | 35 | 50 | 35 | 50 | 35 |
| 59 | 500 | 85 | 85 | 95 | 0 | 95 | 75 | 85 | 80 | 20 | 25 | 30 | 45 | 85 | 5 |
| 60 | 2000 | 0 | 0 | 85 | 85 | 50 | 80 | 50 | 35 | 0 | 10 | 0 | 0 | 40 | 20 |
| 61 | 2000 | 0 | 0 | 80 | 80 | 90 | 70 | 80 | 85 | 20 | 50 | 0 | 85 | 50 | 20 |
| 62 | 2000 | 50 | 20 | 80 | 80 | 80 | 80 | 30 | 50 | 10 | 0 | 0 | 30 | 0 | 0 |
| 63 | 2000 | 0 | 0 | 85 | 90 | 30 | 30 | 20 | 50 | 0 | 25 | 10 | 0 | 20 | 10 |
| 65 | 2000 | 0 | 40 | 70 | 90 | 20 | 20 | 20 | 0 | 0 | 0 | 0 | 0 | 0 | 0 |
| 67 | 1000 | 40 | 30 | 80 | 60 | 55 | 75 | 70 | — | 80 | 78 | 80 | 80 | 30 | 65 |

Example 8

Preemergence of Herbicidal Activity

Seeds of the desired test plant species were planted in sandy soil having a pH range of about 5–7.5 and an organic matter content of less than 1.0 percent in plastic pots with a surface area of 103 square cm. The pots were maintained in a greenhouse with an approximately 14 hr photoperiod maintained at about 25°–33° C. during the day and 15°–20° C. during the night. Nutrients were added on a regular basis and supplemental lighting was provided with an overhead 1000 Watt multi-vapor lamp when necessary.

A weighed amount of each test compound in a 10 mL glass vial was dissolved in 8 mL of a 97:3 mixture of acetone and dimethyl sulfoxide to obtain concentrated solution of known concentration was sprayed evenly onto the soil of seeded pots using a Cornwall TM glass syringe fitted with a TeeJet TM TN-3 hollow cone nozzle so as to obtain thorough coverage with a known amount of each test compound. Control plants were sprayed in the same manner with the aqueous mixture.

The treated plants and control plants were placed in a greenhouse as described above and watered by top-irrigation. After 3 weeks the condition of the test plants compared to that of the untreated plants was determined visually and scored on a scale of 0 to 100 percent, where 0 corresponds to no injury and 100 corresponds to complete kill. Some of the compounds tested, application rates employed, plant species tested, and results are given in Table III.

TABLE III

PREEMERGENCE HERBICIDAL ACTIVITY

| Cpd. No. | Dose Rate, Kg/Ha | Morning-glory | Pig-weed | Velvet-leaf | Wild Buck-wheat | Black grass | Barnyard Grass | Giant Foxtail | Johnson-grass | Corn | Wheat |
|---|---|---|---|---|---|---|---|---|---|---|---|
| 3  | 2.24 | 90  | 90  | 90 | 85  | 85 | 70 | 60 | —  | 95 | 75  |
| 15 | 2.24 | 85  | 100 | 30 | 100 | 95 | 80 | 80 | 95 | 95 | 100 |
| 17 | 2.24 | 0   | 60  | 0  | 0   | 0  | 0  | 0  | 0  | 0  | 0   |
| 19 | 2.24 | 95  | 95  | 85 | 80  | 75 | 70 | 50 | 95 | 75 | 75  |
| 21 | 2.24 | 85  | 100 | 70 | 100 | 55 | 75 | 15 | 65 | 90 | 0   |
| 23 | 4.48 | 50  | 90  | 30 | 90  | 50 | 40 | 20 | 30 | 20 | 0   |
| 27 | 4.48 | 115 | 100 | 0  | 75  | 45 | 75 | 50 | 65 | 25 | 10  |
| 31 | 4.48 | 65  | 95  | 0  | 45  | 0  | 15 | 0  | —  | 0  | 0   |
| 39 | 4.48 | 20  | 30  | 20 | 70  | 40 | 20 | 40 | 0  | 20 | 0   |
| 40 | 4.48 | 80  | 95  | 40 | —   | 60 | 90 | 70 | 75 | 95 | 70  |
| 41 | 1.12 | 90  | 98  | 95 | —   | 80 | 50 | 50 | 75 | 90 | 70  |
| 42 | 2.24 | 90  | 98  | 85 | —   | 90 | 70 | 75 | 80 | 95 | 70  |
| 43 | 2.24 | 85  | 95  | 90 | —   | 85 | 85 | 85 | 85 | 95 | 70  |
| 44 | 4.48 | 60  | 98  | 30 | —   | 80 | 75 | 40 | 85 | 90 | 75  |
| 45 | 4.48 | 70  | 90  | 50 | 50  | 80 | 20 | 40 | 50 | 70 | 30  |
| 46 | 4.48 | 30  | 50  | 0  | 70  | 70 | 30 | 0  | 70 | 20 | 10  |
| 49 | 4.48 | 90  | 100 | 70 | —   | 20 | 0  | 20 | 0  | 40 | 10  |
| 51 | 4.48 | 75  | 95  | 95 | 50  | 70 | 40 | 30 | 90 | 40 | 20  |
| 54 | 4.48 | 20  | 90  | 20 | 80  | 0  | 0  | 0  | 40 | 0  | 10  |
| 59 | 4.48 | —   | 95  | 60 | —   | 60 | 40 | 30 | 60 | 60 | 30  |

What is claimed is:

1. A compound of the formula

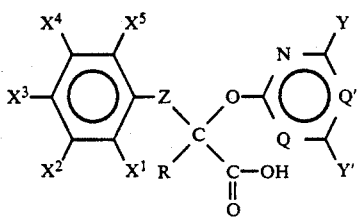

wherein
Q and Q' both represent N;
Y and Y' each independently represent H, $R^1$, $OR^1$, $SR^1$, $NR^2_2$, F, Cl, or Br;
$X^1$ and $X^5$ each independently represent H, F, Cl, Br, or $(C_1-C_4)$alkyl optionally mono- or disubstituted with fluorine;
$X^2$ and $X^4$ each independently represent H, F, Cl, Br, $(C_1-C_4)$alkyl optionally mono- or disubstituted with fluorine, $SR^1$, $OR^1$, or O-phenyl, O-pyridinyl, or O-pyrimidinyl each optionally substituted with up to two substituents selected from F, Cl, Br, $CF_3$, $CH_3$, and CN;
$X^3$ represents H or F;
with the proviso that of $X^1$, $X^2$, $X^3$, $X^4$, and $X^5$ at least two represent H and at least three represent H or F;
Z represents O or S;
R represents H, $(C_1-C_3)$alkyl, $CO_2H$, CN, $CF_3$, or F;
$R^1$ represents $(C_1-C_3)$alkyl optionally singly to completely substituted with fluorine; and
$R^2$ represents H or $(C_1-C_3)$alkyl;
or an agriculturally acceptable salt, ester, or amide thereof.

2. A compound according to claim 1 wherein Z represents O.

3. A compound according to claim 1 wherein $X^1$ represents F and $X^2$, $X^3$, $X^4$, and $X^5$ represent H; wherein $X^2$ represents F and $X^1$, $X^3$, $X^4$, and $X^5$ represent H; or wherein $X^1$ and one of $X^4$ and $X^5$ represent F and $X^2$, $X^3$ and the other of $X^4$ and $X^5$ represent H.

4. A compound according to claim 1 wherein Y and Y' each independently represent H, $CH_3$, or $OCH_3$.

5. A compound according to claim 1 wherein R represents H.

6. A compound according to claim 1 in the form of an agriculturally acceptable salt, ester, or amide.

7. A compound according to claim 6 wherein the compound is in the form of a $(C_1-C_8)$alkyl or $(C_3-C_8)$alkoxyalkyl ester.

8. A compound according to claim 6 which is an agriculturally acceptable ester of 2-(2-fluorophenoxy)-2-(4,6-dimethyl-1,3,5-triazin-2-yloxy)acetic acid.

9. An herbicidal composition comprising an agriculturally acceptable adjuvant or carrier in admixture with an herbicidal amount of a compound of the formula

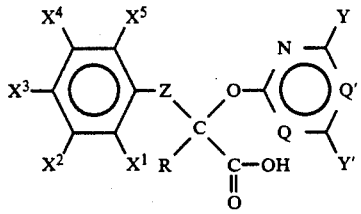

wherein
Q and Q' both represent N;
Y and Y' each independently represent H, $R^1$, $OR^1$, $SR^1$, $NR^2_2$, F, Cl, or Br;
$X^1$ and $X^5$ each independently represent H, F, Cl, Br, or $(C_1-C_4)$alkyl optionally mono- or disubstituted with fluorine;
$X^2$ and $X^4$ each independently represent H, F, Cl, Br, $(C_1-C_4)$alkyl optionally mono- or disubstituted with fluorine, $SR^1$, $OR^1$, or O-phenyl, O-pyridinyl, or O-pyrimidinyl each optionally substituted with up to two substituents selected from F, Cl, Br, $CF_3$, $CH_3$, and CN;
$X^3$ represents H or F;
with the proviso that of $X^1$, $X^2$, $X^3$, $X^4$, and $X^5$ at least two represent H and at least three represent H or F;
Z represents O or S;
R represents H, $(C_1-C_3)$alkyl, $CO_2H$, CN, $CF_3$, or F;
$R^1$ represents $(C_1-C_3)$alkyl optionally singly to completely substituted with fluorine; and
$R^2$ represents H or $(C_1-C_3)$alkyl;

or an agriculturally acceptable salt, ester, or amide thereof.

10. A composition according to claim 9 wherein Z represents O.

11. A composition according to claim 9 in the form of an agriculturally acceptable salt, ester, or amide.

12. A composition according to claim 11 wherein Z represents O; both Q and Q' represent N; $X^1$ represents F and $X^2$, $X^3$, $X^4$, and $X^5$ represent H or $X^2$ represents F and $X^1$, $X^3$, $X^4$, and $X^5$ represent H, or $X^1$ and one of $X^4$ and $X^5$ represent F and $X^2$, $X^3$ and the other of $X^4$ and $X^5$ represent H; Y and Y' each independently represent H, $CH_3$, or $OCH_3$; and R represents H.

13. A method of controlling undesirable vegetation which comprises contacting the vegetation or the locus thereof with an herbicidal amount of a compound of the formula

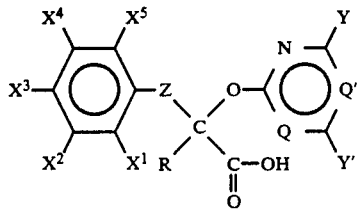

wherein
Q and Q' both represent N;
Y and Y' each independently represent H, $R^1$, $OR^1$, $SR^1$, $NR^2_2$, F, Cl, or Br;
$X^1$ and $X^5$ each independently represent H, F, Cl, Br, or $(C_1-C_4)$alkyl optionally mono- or disubstituted with fluorine;
$X^2$ and $X^4$ each independently represent H, F, Cl, Br, $(C_1-C_4)$alkyl optionally mono- or disubstituted with fluorine, $SR^1$, $OR^1$, or O-phenyl, O-pyridinyl, or O-pyrimidinyl each optionally substituted with up to two substituents selected from F, Cl, Br, $CF_3$, $CH_3$, and CN;
$X^3$ represents H or F;
with the proviso that of $X^1$, $X^2$, $X^3$, $X^4$, and $X^5$ at least two represent H and at least three represent H or F;
Z represents O or S;
R represents H, $(C_1-C_3)$alkyl, $CO_2H$, CN, $CF_3$, or F;
$R^1$ represents $(C_1-C_3)$alkyl optionally singly to completely substituted with fluorine; and
$R^2$ represents H or $(C_1-C_3)$alkyl;
or an agriculturally acceptable salt, ester, or amide thereof.

14. A method according to claim 13 wherein Z represents O.

15. A method according to claim 13 wherein the compound is in the form of an agriculturally acceptable salt, ester, or amide.

16. A method according to claim 15 wherein Z represents O; both Q and Q' represent N; $X^1$ represents F and $X^2$, $X^3$, $X^4$, and $X^5$ represent H or $X^2$ represents F and $X^1$, $X^3$, $X^4$, and $X^5$ represent H, or $X^1$ and one of $X^4$ and $X^5$ represent F and $X^2$, $X^3$ and the other of $X^4$ and $X^5$ represent H; Y and Y' each independently represent H, $CH_3$, or $OCH_3$; and R represents H.

* * * * *